US012758412B2

(12) United States Patent
Grenier et al.

(10) Patent No.: US 12,758,412 B2

(45) Date of Patent: Oct. 13, 2026

(54) KNEE ORTHOSIS

(71) Applicant: OSSKIN ORTHO INC., Montréal (CA)

(72) Inventors: Victor Grenier, Montréal (CA); Pierre Coutu, Montréal (CA); Etienne Marquis, Montréal (CA)

(73) Assignee: OSSKIN ORTHO INC., Montréal (CA)

( * ) Notice: Subject to any disclaimer, the term of this patent is extended or adjusted under 35 U.S.C. 154(b) by 109 days.

(21) Appl. No.: 18/660,873

(22) Filed: May 10, 2024

(65) Prior Publication Data

US 2024/0374411 A1 Nov. 14, 2024

Related U.S. Application Data

(60) Provisional application No. 63/501,798, filed on May 12, 2023.

(51) Int. Cl.
*A61F 5/01* (2006.01)

(52) U.S. Cl.
CPC .... *A61F 5/0123* (2013.01); *A61F 2005/0137* (2013.01)

(58) Field of Classification Search
CPC .... A61F 5/0102; A61F 5/0123; A61F 5/0125; A61F 5/013; A61F 2005/0137; A61F 2005/0165; A61F 2005/0132; A61H 1/024
See application file for complete search history.

(56) References Cited

U.S. PATENT DOCUMENTS 5,107,824 A * 4/1992 Rogers .................. A61F 5/0123 602/26

FOREIGN PATENT DOCUMENTS

| | | |
|---|---|---|
| CA | 2169435 | 8/1997 |
| WO | 9409729 | 5/1994 |
| WO | 2007110050 | 10/2007 |
| WO | 2019109178 | 6/2019 |

OTHER PUBLICATIONS

International Search Report and Written Opinion dated Aug. 27, 2024, International Application No. PCT /CA2024/050639.

* cited by examiner

*Primary Examiner* — Alireza Nia
*Assistant Examiner* — Gina Mccarthy
(74) *Attorney, Agent, or Firm* — NORTON ROSE FULBRIGHT CANADA LLP

(57) ABSTRACT

The present knee orthosis includes a femoral cuff configured for engaging an upper leg of a wearer, a tibial cuff configured for engaging a lower leg of the wearer, and a hinge pivotally connecting the femoral cuff to the tibial cuff. The hinge has a femoral portion and a tibial portion that include respective shells engaged with one another and configured to pivot relative to one another about a center of rotation. One of the shells includes an engagement surface facing a complementary engagement surface on the other shell. The engagement surface and the complementary engagement surface each have a shape corresponding to a portion of an ellipsoid defined by: a major axis extending in a sagittal plane; a minor axis orthogonal to the major axis; a length of the ellipsoid along the major axis being greater than a length along the minor axis; and revolution around the major axis.

23 Claims, 15 Drawing Sheets

KNEE ORTHOSIS

CROSS-REFERENCE TO RELATED APPLICATIONS

The present application claims priority on U.S. patent application No. 63/501,798 filed May 12, 2023, the entire contents of which are incorporated herein by reference.

TECHNICAL FIELD

The present disclosure relates generally to knee braces and/or knee orthoses.

BACKGROUND

Knee orthoses are externally applied devices used to influence the structural and functional characteristics of the neuromuscular and skeletal systems. A knee orthosis is a brace that extends above and below the knee joint and is generally worn to support or align the knee during flexion thereof. In the case of conditions affecting the ligaments or cartilage of the knee, a knee orthosis can provide stabilization to the knee by replacing or assisting the function of these injured or damaged ligaments or cartilage of the knee. For instance, knee braces can be used to relieve pressure from the part of the knee joint affected by diseases such as arthritis or osteoarthritis by realigning the knee joint into valgus or varus. In this way a knee orthosis may help reduce osteoarthritis pain. When used properly, a knee brace may also help a wearer to stay active by enhancing the position and movement of the knee or reducing pain.

Knee orthoses have been developed to follow the knee's natural center of rotation, which changes position during flexion of the knee. Put differently, the center of rotation of the knee changes position as the knee flexes, and knee orthoses have been developed to follow and support the natural movement of the knee during flexion.

However, in spite of previous efforts, there exists room for improvement in the art of knee orthoses.

SUMMARY

It should be understood that any or all of the features, aspects or embodiments described herein can be used or combined in any combination with each and every other feature or embodiment described, unless expressly noted otherwise.

In accordance with one aspect, there is provided a knee orthosis comprising: a femoral cuff configured for engaging an upper leg of a wearer; a tibial cuff configured for engaging a lower leg of the wearer; a hinge pivotally connecting the femoral cuff to the tibial cuff, the hinge having a femoral portion connected to the femoral cuff and a tibial portion connected to the tibial cuff, the femoral portion and the tibial portion including respective shells engaged with one another and configured to pivot relative to one another about a center of rotation, a first one of the shells including an engagement surface facing a complementary engagement surface on a second one of the shells, the engagement surface and the complementary engagement surface each having a shape corresponding to a portion of an ellipsoid defined by: a major axis extending in a sagittal plane; a minor axis orthogonal to the major axis; a length of the ellipsoid along the major axis being greater than a length along the minor axis; and revolution around the major axis.

The knee orthosis as defined above and described herein may also include one or more of the following features, in whole or in part, and in any combination.

In some implementations, the major axis corresponds to an anteroposterior axis, and the major axis is disposed in the sagittal plane at a pre-determined angle relative to a frontal plane orthogonal to the sagittal plane.

In some implementations, the pre-determined angle is between 40 and 80 degrees.

In some implementations, the length of the ellipsoid along the minor axis is determined based on a morphologic feature of a knee of the wearer.

In some implementations, the morphologic feature is a width of the knee of the wearer.

In some implementations, the length of the ellipsoid along the major axis is greater than the length of the ellipsoid along the minor axis by an amount corresponding to an anteroposterior shift of a center of rotation of the knee.

In some implementations: at a mid-flexion point configuration of the hinge, the shells have a first interference therebetween, at a starting point flexion configuration, the shells have a second interference therebetween; at an end point flexion configuration, the shells have a third interference therebetween; and the first interference is smaller than at least one of the second and third interference.

In some implementations, one of the femoral and tibial portions of the hinge has at least one guide slot defined in the corresponding shell, another one of the femoral portion and the tibial portion has at least one pin extending in the at least one guide slot for guiding a pivot of the femoral and tibial portions relative to one another, the at least one pin defining an axis intersecting a center of rotation of a knee of the wearer.

In some implementations: the hinge includes two or three guide slots and two or three pins; said two or three guide slots being located on the femoral portion, the tibial portion or a combination of the two; and said two or three pins being located on the femoral portion, the tibial portion or a combination of the two.

In some implementations, the femoral portion of the hinge has at least one guide slot and at least one pin, and the tibial portion of the hinge has at least one guide slot and at least one pin.

In some implementations, the center of rotation is an instantaneous center of rotation at a given flexion configuration of the hinge, the instantaneous center of rotation moving along a trajectory during flexion of the hinge.

In some implementations, the center of rotation is an instantaneous center of rotation at a given flexion configuration of the hinge, the instantaneous center of rotation moving along a trajectory during flexion of the hinge, and wherein the axis of the at least one pin intersects the instantaneous center of rotation regardless of the flexion configuration of the hinge.

In some implementations, the trajectory is contained in the sagittal plane.

In accordance with another aspect, there is also provided a knee orthosis comprising: a femoral cuff configured for engaging an upper leg of a wearer; a tibial cuff configured for engaging a lower leg of the wearer; and a hinge pivotally connecting the femoral cuff to the tibial cuff, the hinge having a femoral portion connected to the femoral cuff and a tibial portion connected to the tibial cuff, the femoral portion and the tibial portion including corresponding shells engaged with one another and configured to pivot relative to one another about a center of rotation, one of the femoral portion and the tibial portion has at least one guide slot defined in the corresponding shell, and the other of the femoral portion and the tibial portion has at least one pin extending therefrom and received within the at least one guide slot for guiding the pivot of the femoral and tibial portions relative to one another, the at least one pin defining a pin axis intersecting a center of rotation of a knee of the wearer.

The knee orthosis as defined above and described herein may also include one or more of the following features, in whole or in part, and in any combination.

In some implementations, the center of rotation is an instantaneous center of rotation at a given flexion configuration of the hinge, the instantaneous center of rotation moving along a trajectory during flexion of the hinge, and the pin axis intersecting the instantaneous center of rotation regardless of the flexion configuration of the hinge.

In some implementations, the trajectory is contained in a sagittal plane.

In some implementations, the shells have a shape corresponding to a portion of an ellipsoid defined by: a major axis extending in a sagittal plane; a minor axis orthogonal to the major axis; a length of the ellipsoid along the major axis being greater than a length along the minor axis; and revolution around the major axis.

In some implementations, the major axis corresponds to an anteroposterior axis, and the major axis is disposed in the sagittal plane at a pre-determined angle relative to a frontal plane orthogonal to the sagittal plane.

In some implementations, the pre-determined angle is between 40 and 80 degrees.

In some implementations, the length of the ellipsoid along the minor axis corresponds to a morphologic feature of a knee of the wearer.

In some implementations, the morphologic feature is a width of the knee of the wearer.

In some implementations, the length of the ellipsoid along the major axis is greater than the length of the ellipsoid along the minor axis by an amount corresponding to an anteroposterior shift of the center of rotation of the knee.

In some implementations: at a mid-flexion point configuration of the hinge, the shells have a first interference therebetween, at a starting point flexion configuration, the shells have a second interference therebetween; at an end point flexion configuration, the shells have a third interference therebetween; and the first interference is smaller than at least one of the second and third interference.

Further details of these and other aspects of the subject matter of this application will be apparent from the detailed description included below and the drawings.

BRIEF DESCRIPTION OF THE DRAWINGS

Reference is now made to the accompanying drawings, in which.

DETAILED DESCRIPTION

The following disclosure generally describes knee orthoses 20 being embodiments of the present technology. It is to be expressly understood that the knee orthoses 20 are merely embodiments of the present technology. The description thereof that follows is intended to be only a description of physical examples of the present technology. This description is not intended to define the scope or set forth the bounds of the present technology. In some cases, what are believed to be helpful examples of modifications to the knee orthoses 20 are also set forth hereinbelow. This is done merely as an aid to understanding, and not to define the scope or set forth the bounds of the technology. These modifications are not exhaustive, and, as a person skilled in the art would understand, other modifications are likely possible. Further, it should not be interpreted that where this has not been done, i.e. where no examples of modifications have been set forth, that no modifications are possible and/or that what is described is the sole physical means of embodying that element of the present technology. As a person skilled in the art would understand, this is likely not the case.

Figure 1B:
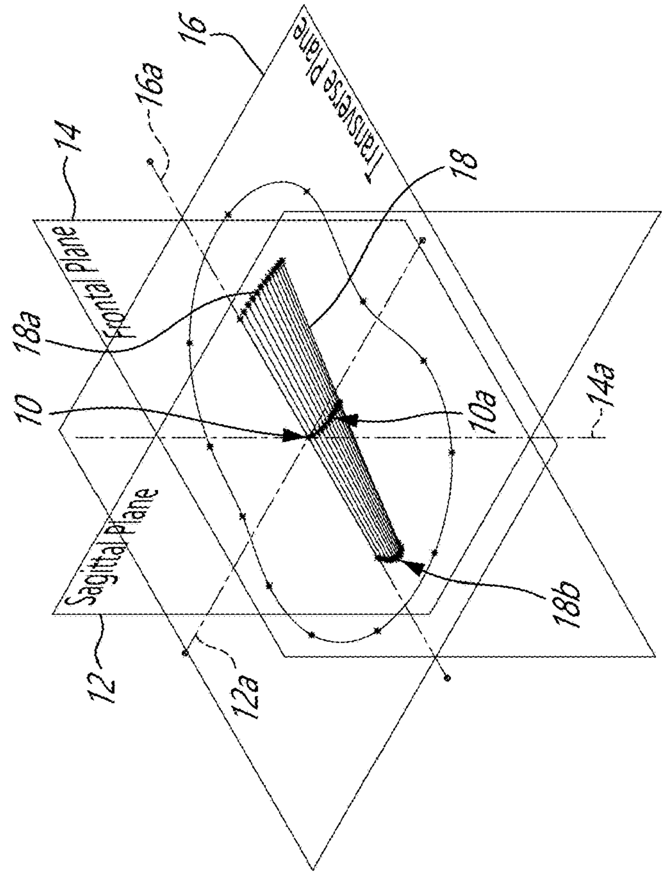
FIG. 1B is an isometric view of the tibial plateau of FIG. 1A.
Figure 1A:
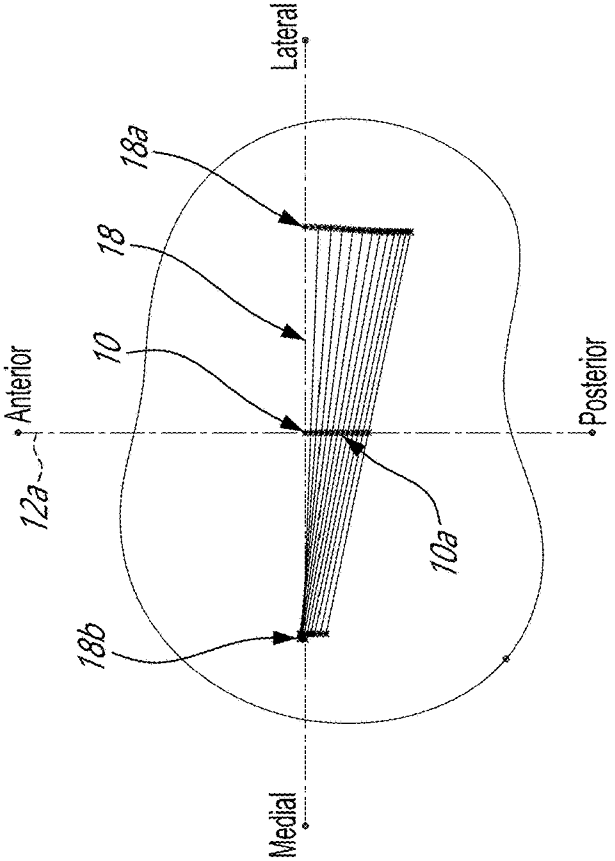
FIG. 1A is a top plan view of a tibial plateau with instantaneous flexion axes represented in 10° increments for a flexion of a knee ranging between 0° and 120°.

Referring to FIGS. 1A-1B, the knee, being one of the most complex joint in the human body, has five degrees of freedom, which are (i) flexion/extension rotation; (ii) adduction/abduction rotation; (iii) external/internal rotation; (iv) anteroposterior translation; and (v) superior/inferior translation. There can be determined the axes' center of rotation 10 for, for example, 5° increments between 0 and 120° of flexion of the knee and the lateral and medial extremities positions that define the axis' orientation for every increment. The instantaneous center of rotation (COR) 10 moves during flexion of the knee along a trajectory 10*a* that is contained in the sagittal plane 12. Put differently, the knee's biomechanical COR 10 translates on the trajectory 10*a* along an anteroposterior axis 12*a* extending in a sagittal plane 12 and an infero-superior axis 14*a* (projecting in/out of the sheet including FIG. 1A). In the following description, reference is made to the sagittal plane 12, a frontal plane 14, and a transversal plane 16 (i.e. contained in the sheet including FIG. 1A), all orthogonal to one another. More particularly, the anteroposterior axis 12*a* lies at the intersection of the sagittal plane 12 with the transversal plane 16. A mediolateral axis 16*a* lies at the intersection of the frontal plane 14 and the transversal plane 16. The knee's COR 10 is at the center of an instantaneous flexion axis 18, which extends between a lateral condyle center 18*a* and a medial condyle center 18*b*.

Referring to FIGS. 2 to 9C, the knee orthosis 20 will be described. As will become apparent from the following description, the knee orthosis 20 has features designed to constrain the knee during flexion therefor and accommodates for rotation and translation kinematics with respect to the knee's instantaneous flexion angle, and thus prevent movement of the knee outside a pre-determined range of motion. In other words, the knee orthosis 20 has features designed to have the knee orthosis 20 closely follow the knee's COR 10.

Figure 2:
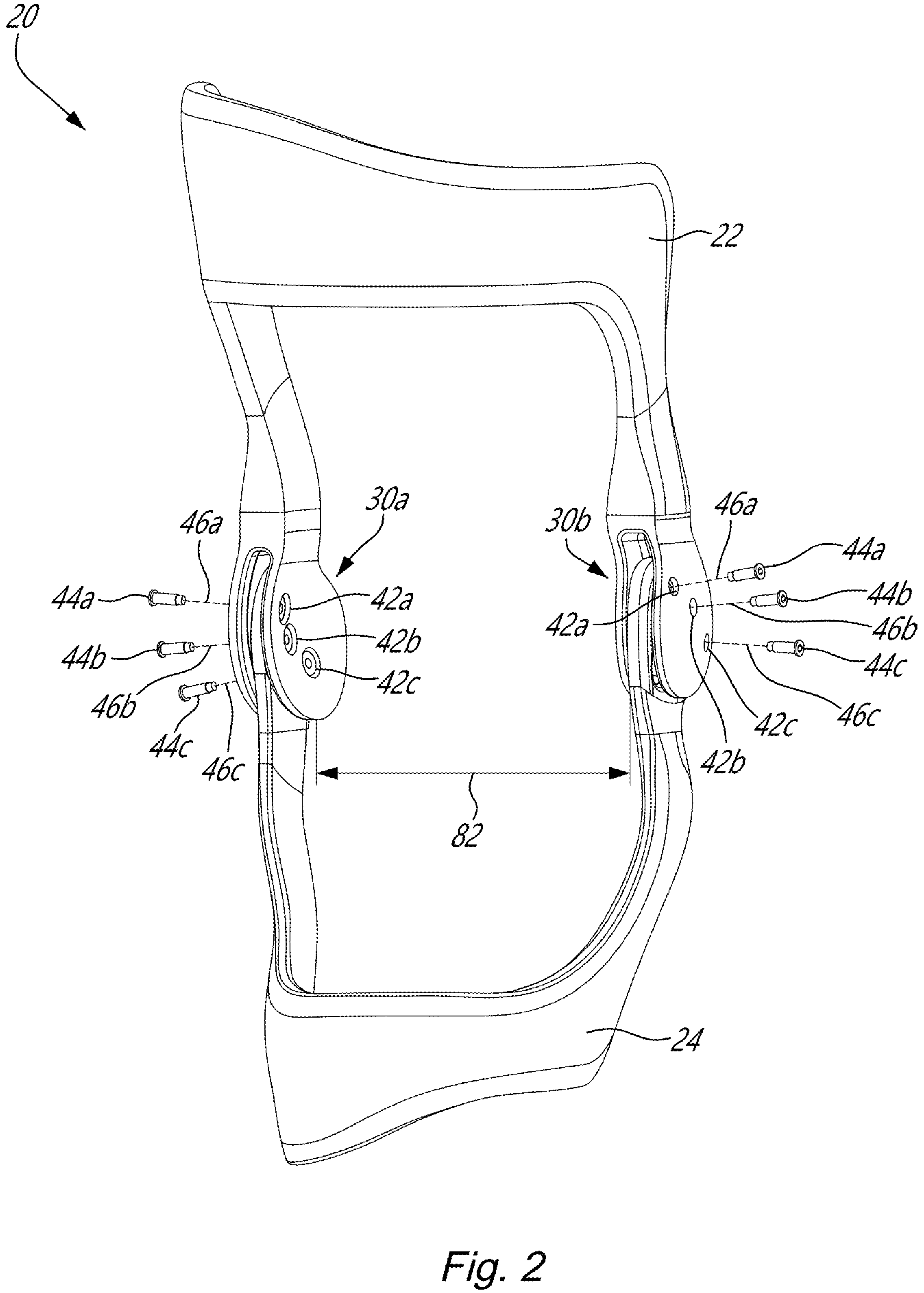
FIG. 2 is an isometric view of a knee orthosis in accordance with one implementation of the present technology.

Turning now to FIG. 2, the knee orthosis 20 has a femoral cuff 22 configured for engaging a femur of a wearer of the knee orthosis 20, a tibial cuff 24 configured for engaging a tibia of the wearer, and hinges 30*a*, 30*b* pivotally connecting the femoral cuff 22 to the tibial cuff 24. The hinges 30*a*, 30*b* will be described in detail below. However, as will be explained herein, the hinges 30*a*, 30*b* are formed by complementary shells having ellipsoidal engagement surfaces. The lateral hinge 30*a* and the medial hinge 30*b* are asymmetrical about the sagittal plane 12, whereby the outlines of each of the opposed hinges and the shapes of the slots defined in each of the hinges (which will be described in further detail below) are not symmetrical about the sagittal plane 12. The term "asymmetrical" as used herein with respect to the lateral and medial hinges 30*a*, 30*b* is understood to be defined in this manner. It is to be understood, however, that certain surfaces (such as a curvature of the shells) may nevertheless be symmetric about the sagittal plane 12, while the lateral and medial hinges 30*a*, 30*b* remain asymmetric. The asymmetrical nature of the lateral hinge 30*a* and the medial hinge 30*b* permits the knee to travel through a selected flexion movement when wearing the knee orthosis 20. This selected movement of the knee may in some cases biomechanically correspond to the natural movement of the knee. However, in other cases it may be desired to select a movement controlled by the knee orthosis 20 that deviates from the natural movement of the knee, which may be desired.

The knee orthosis 20 as described herein, and more particularly the hinges 30*a*, 30*b* thereof, permit five degrees of freedom to be guided, excluding the medial-lateral displacement, and also permit the amplitude of the movement in each of these degrees of freedom to be controlled, and this as a function of the flexion angle of the knee. Namely, expected ranges for each respective degree of freedom of the tibia relative to the femur throughout full flexion could be as follows: Adduction(−)-Abduction(+) is from 0 to 7.5°; External(−)-Internal(+) rotation is from 0 to 15°; Medio(−)-lateral(+) translation is from −5 mm to +5 mm; Antero(+)-Posterior(−) translation is from 0 to 15 mm; and Proximo(+)-Distal(−) translation is −5 mm to 10 mm.

Referring still to FIG. 2, the femoral and tibial cuffs 22, 24 of the knee orthosis 20 may be dimensioned and/or adapted to conform to morphologic feature(s) of the wearer. The cuffs 22, 24 may be manufactured using injection molding techniques, and be manufactured in different sizes and configurations. In some implementations, the cuffs 22, 24 are made using additive manufacturing techniques and based on a model of the wearer's knee obtained based on a scan and/or measurements of the wearer's knee. Such an implementation may provide for a custom fit of the femoral and tibial cuffs 22, 24, and may improve wearer's comfort.

Still referring to FIG. 2, the hinges 30*a*, 30*b* include a lateral hinge 30*a* and a medial hinge 30*b*. The hinges 30*a*, 30*b* have similar construction and features, and will be described collectively in the following description, unless indicated otherwise. It is contemplated that the knee orthosis 20 could include only one hinge, whether medial or lateral, and therefore be single-sided. The hinges 30*a*, 30*b* are provided as separate component from the cuffs 22, 24, but could have portions thereof integrally formed with the cuffs 22, 24.

Figure 3B:
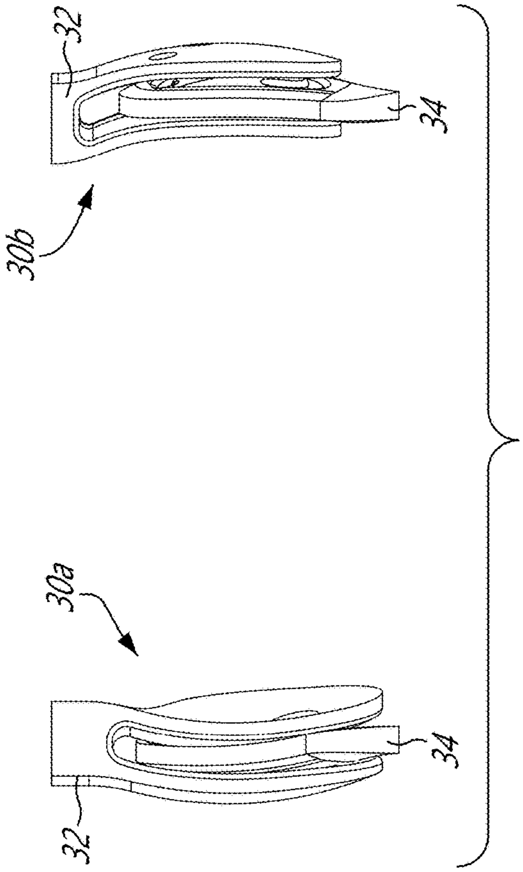
FIG. 3B is a front view of the hinges of FIG. 3A.
Figure 3C:
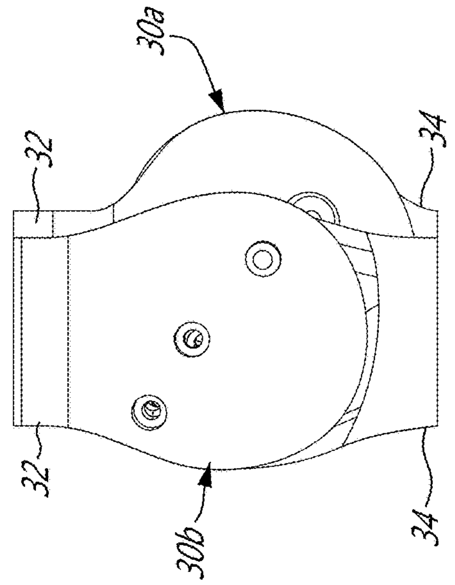
FIG. 3C is a side view of the hinges of FIG. 3A.
Figure 3A:
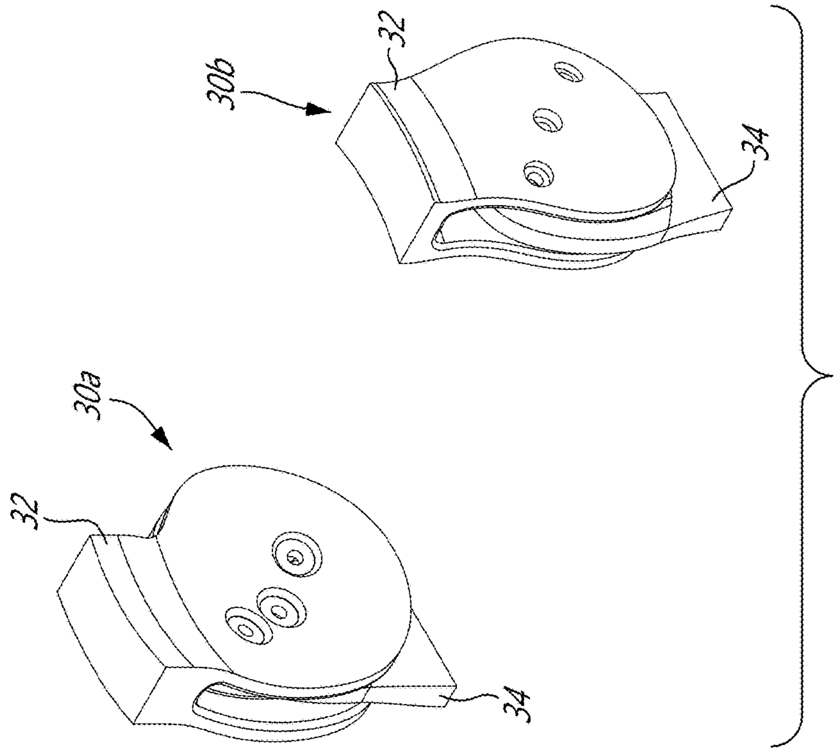
FIG. 3A is an isometric view of lateral and medial hinges of the knee orthosis of FIG. 2.
Figure 4B:
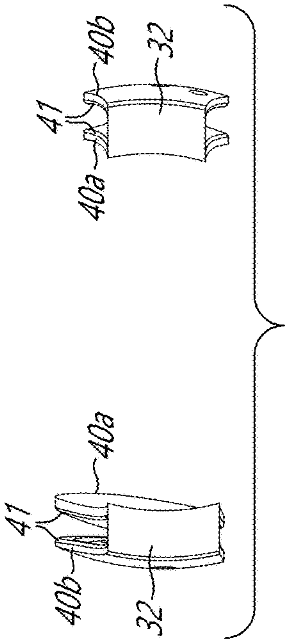
FIG. 4B is a top view of the femoral portions of FIG. 4A.
Figure 4C:
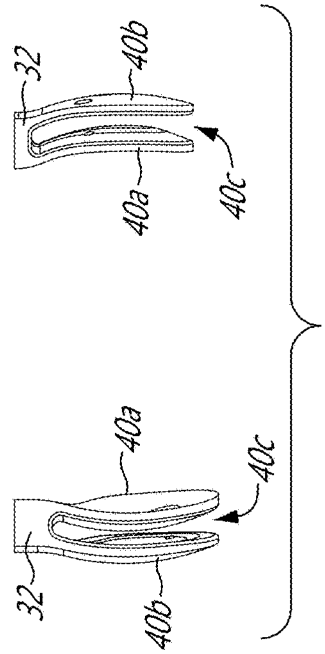
FIG. 4C is a front view of the femoral portions of FIG. 4A.
Figure 4E:
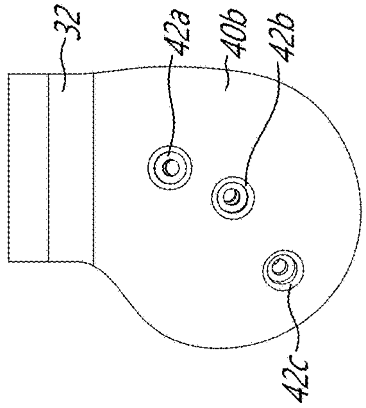
FIG. 4E is a side view of the medial femoral portion of FIG. 4A.
Figure 4D:
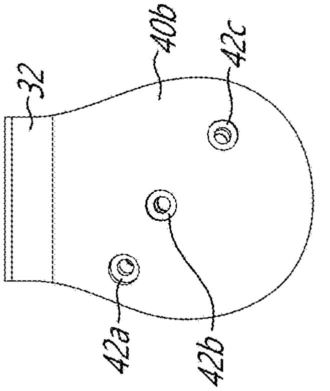
FIG. 4D is a side view of the lateral femoral portion of FIG. 4A.
Figure 4A:
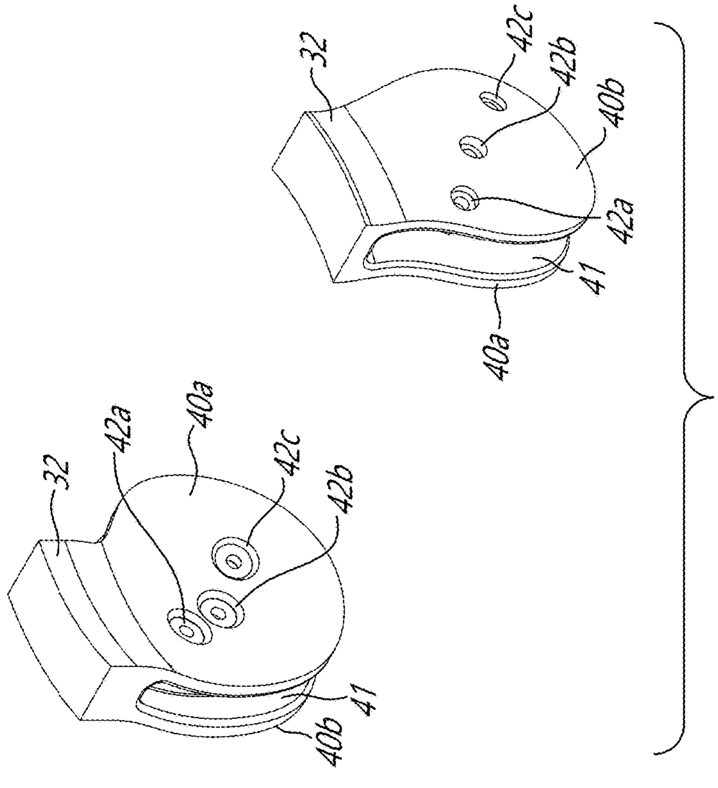
FIG. 4A is an isometric view of femoral portions of the hinges of FIG. 3A.
Figure 5B:
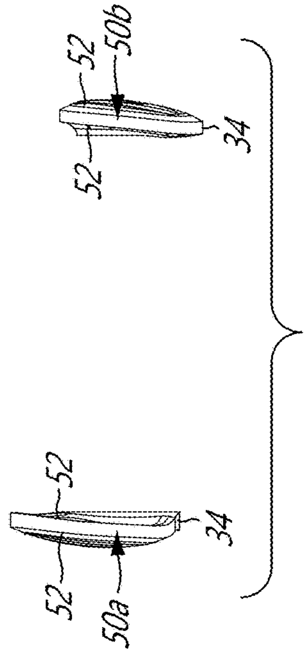
FIG. 5B is a top view of the tibial portions of FIG. 5A.
Figure 5C:
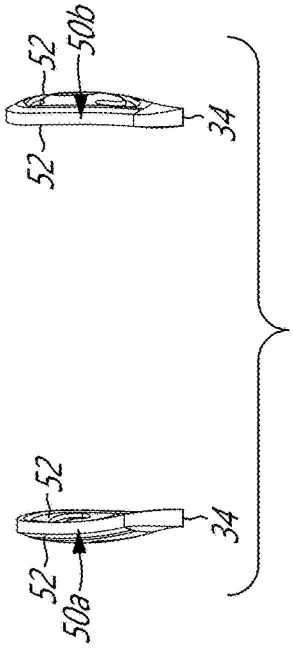
FIG. 5C is a front view of the tibial portions of FIG. 5A.
Figure 5D:
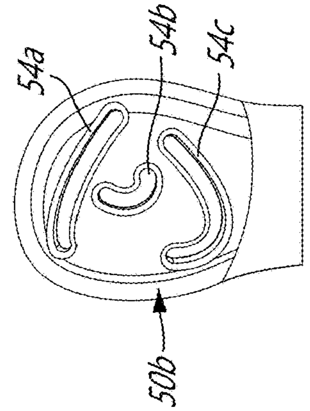
FIG. 5D is a side view of the medial tibial portion of FIG. 5A.
Figure 5E:
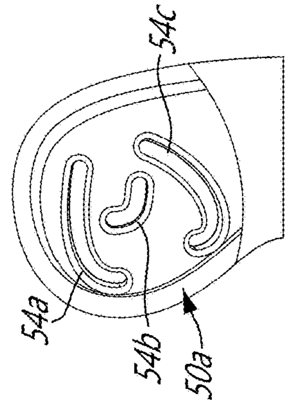
FIG. 5E is a side view of the lateral tibial portion of FIG. 5A.
Figure 5A:
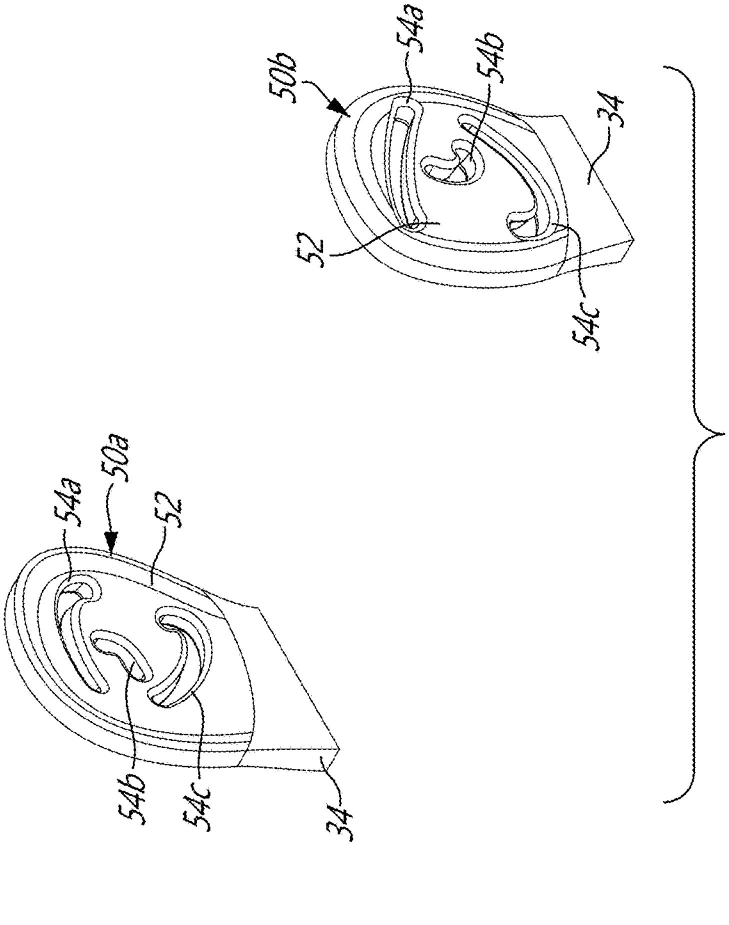
FIG. 5A is an isometric view of tibial portions of the hinges of FIG. 3A.

Referring to FIGS. 3A-3C, each one of the hinges 30*a*, 30*b* has a femoral portion 32 configured for connection to the femoral cuff 22, and a tibial portion 34 configured for connection to the tibial cuff 24. The femoral and tibial portions 32, 34 are connected to the corresponding cuff 22, 24 by a suitable attachment means, which may include for example fasteners, welding, bonding, and/or adhesives, and the like. Having the hinges 30*a*, 30*b* provided as separate components from the cuffs 22, 24 allows for matching adequately sized or custom made cuffs 22, 24 with hinges 30*a*, 30*b* that may be manufactured using other manufacturing techniques, such as machining or additive manufacturing, or using material(s) that differ from the one(s) forming the cuffs 22, 24. The hinges 30*a*, 30*b* allow the femoral cuff 22 and the tibial cuff 24 to pivot relative to one another during flexion of the knee. More particularly, the hinges 30*a*, 30*b* are configured for allowing femoral roll back and screw home motions during flexion and extension of the knee.

Referring to FIGS. 4A-4E, the femoral portion 32 of the hinges 30*a*, 30*b* are shown. In the depicted embodiment, the femoral portion 32 has, on both the medial and lateral sides, spaced apart inner and outer shells 40*a*, 40*b*. However, it is to be understood that alternately, the femoral portion 32 may have only one shell, which is received within a gap defined between two shells which form part of the tibial portion 34. In other words, in this alternate embodiment, each hinge is effectively upside down relative to the hinges 30*a*, 30*b* as shown. In the embodiment of FIGS. 4A-4E, however, the inner shell 40*a* is located closer to the knee of the wearer, while the outer shell 40*b* is located further away from the knee of the wearer. The shells 40*a*, 40*b* extend parallel to one another and are offset to define a gap 40*c* (FIG. 4C) therebetween.

The engagement surfaces 41 (see FIG. 4B) of the shells 40*a*, 40*b* (i.e., the femoral shells) have a shape corresponding to a portion of an ellipsoid 60 (FIG. 8D), and this feature will be described in detail below. The engagement surfaces 41 of the shells 40*a*, 40*b* are adapted for engaging with other components of the hinges 30*a*, 30*b*. The engagement surfaces 41 may be polished or have a surface finish adapted for reducing friction or wear when engaging other components of the hinges 30*a*, 30*b*. The engagement surfaces 41 may be defined by consumable, abradable material provided on the shells 40*a*, 40*b*, in some implementations, in order to limit wear the shells 40*a*, 40*b*. The shells 40*a*, 40*b* further defines holes 42*a*, 42*b*, 42*c* adapted for receiving therein a corresponding pin 44*a*, 44*b*, 44*c* (FIG. 2). Each pin 44*a*, 44*b*, 44*c* extends in the gap 40*c*. The pins 44*a*, 44*b*, 44*c* may be provided in the form of fasteners such as screws, rivets or bolts and nuts. Alternately, the pins 44*a*, 44*b*, 44*c* may be integrally formed with the femoral or the tibial shells. The pins 44*a*, 44*b*, 44*c* define respective pin axes 46*a*, 46*b*, 46*c* (see FIGS. 7A-7F), each pin axis extending centrally and longitudinally through a respective one of the pins.

Referring to FIGS. 5A-5E, the tibial portion 34 of the hinges 30*a*, 30*b* are shown. The tibial portion 34 has shells 50*a*, 50*b* (i.e., the tibial shells) adapted for insertion in the gap 40*c*. The shells 50*a*, 50*b* define engagement surfaces 52 which, like the engagement surfaces 41 of the femoral shells 40*a*, 40*b*, also have a shape corresponding to a portion of an ellipsoid 60 (FIG. 8D), and this feature will be described in detail below. The engagement surfaces 52 of the tibial shells 50*a*, 50*b* having an ellipsoidal shape are adapted for sliding on the complementarily ellipsoidal shaped engagement surfaces 41 of the inner and outer shells 40*a*, 40*b* of the femoral portion 32. The engagement surfaces 52 may also be polished or have a surface finish adapted for reducing friction or wear when engaging the engagement surfaces 41. The engagement surfaces 52 may also be defined by consumable, abradable material provided on the shells 50*a*, 50*b*, in some implementations, in order to limit wear the shells 50*a*, 50*b*. The shells 50*a*, 50*b* further define guide slots 54*a*, 54*b*, 54*c* adapted for receiving a corresponding one of the pins 44*a*, 44*b*, 44*c* therein. The guide slots 54*a*, 54*b*, 54*c* are adapted for guiding the pivot of the femoral and tibial portions 32, 34 relative to one another during flexion of the knee orthosis 20. The guide slots 54*a*, 54*b*, 54*c* are defined by tracking projections about the instantaneous flexion axis 18 on the ellipsoid 60 throughout a full flexion range of the knee orthosis 20.

More particularly, the geometry of the guide slots is chosen such that the relative movement between the guide slots and the pins generate a predetermined rotation about a virtual flexion axis, at each of a plurality of points through the range of travel, as the knee orthosis moves through its full flexion range, such as to cause a desired movement of the knee (i.e. the 5 DOFs of the femur relative to the tibia). Stated differently, the relative positions of each pin in their respective slots at a given instant define an instantaneous axis of rotation. At each of a plurality of points along the travel paths exists such a corresponding instantaneous axis of rotation defined by the slots, as the knee orthosis moves through its full flexion range. This plurality of points accordingly correspond to a respective plurality of flexion angles of the knee orthosis, at each of this plurality of points, as the hinges pivot through the full flexion range of the knee orthosis. The hinge's slots are designed such as their instantaneous axes of rotation and corresponding flexion angles collectively define the instantaneous flexion axes of the desired movement of the knee. A chosen relative positions of the pin axes can thus be projected onto the ellipsoidal shells around each corresponding axis of rotation and flexion angle of the desired movement of the knee to trace the travel paths of the guide slots.

In the present implementation, sidewalls of the tibial portion 34 defining the guide slots 54*a*, 54*b*, 54*c* extend parallel to the corresponding axis 46*a*, 46*b*, 46*c*. In other implementations, the sidewalls could have a convex, arcuate shape to allow rocking movement of the pins 44*a*, 44*b*, 44*c* when moving within the corresponding guide slot 54*a*, 54*b*, 54*c*.

Although in the embodiment described above the shells 50*a*, 50*b* define three guide slots 54*a*, 54*b*, 54*c* which respectively receive corresponding pins 44*a*, 44*b*, 44*c* therein, it is also contemplated that there could be more or less than three guide slots and corresponding pins in other implementations, depending on the type and amplitude of motion that the knee orthosis 20 is designed to accommodate or restrain. It is also contemplated that the guide slots and pins can be integrated into any mixed configurations, where the guide slots and pins are integrated in either femoral or tibial shells, or a combination of the two. The guide slot(s) and pin(s) can also be integrated into any positional configurations, or permutations, meaning any guide slot can be integrated into either the tibial or femoral shell, with the corresponding pin integrated to the opposing shell.

Figure 6C:
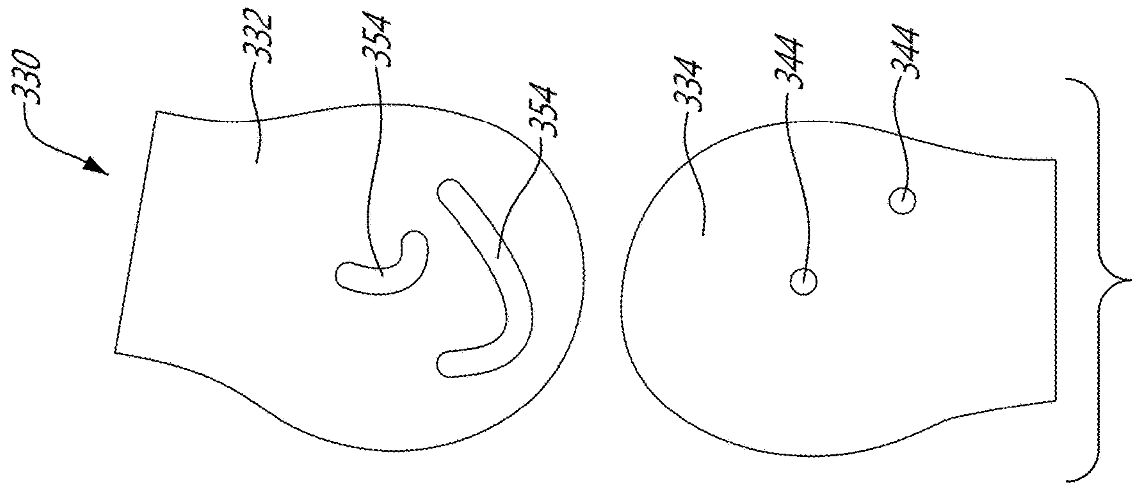
FIGS. 6A-6C show side views of exemplary hinge configurations, showing both a femoral portion and a tibial portion of each hinge, having different combinations and permutations of two pins and two slots.
Figure 6B:
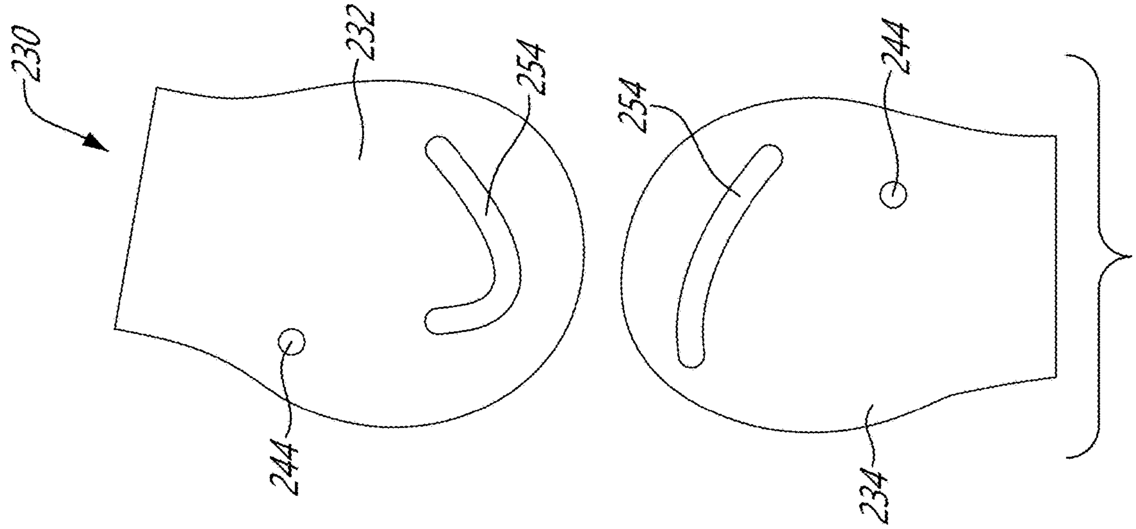
Figure 6A:
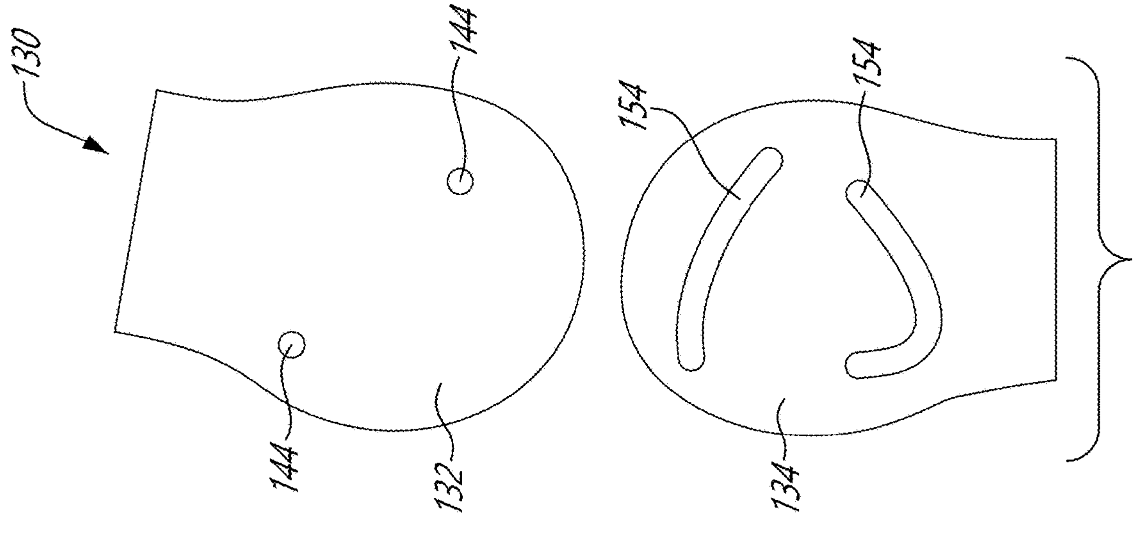

Referring for example to FIGS. 6A-6C, three different hinge configurations are depicted, each having two guide slots and two corresponding pins. In the embodiment of FIG. 6A, the hinge 130 includes two guide slots 154 located in the tibial portion 134 and two pins 144 located on the femoral portion 132. In the embodiment of FIG. 6B, the hinge 230 includes two guide slots 254, one located in the tibial portion 234 and one located in the femoral portion 232, and two pins 244, one located in the tibial portion 234 and one located in the femoral portion 232. In the embodiment of FIG. 6C, the hinge 330 includes two guide slots 354 located in the femoral portion 332 and two pins 344 located on the tibial portion 334. Each of these hinge configurations can also be inversed (e.g., the elements located on the tibial portion being located on the femoral portion, and vice versa). It is also to be understood that these examples are but three possible hinge configurations, and that other alternate configurations and permutations are possible without departing from the scope of the present disclosure.

Figure 6G:
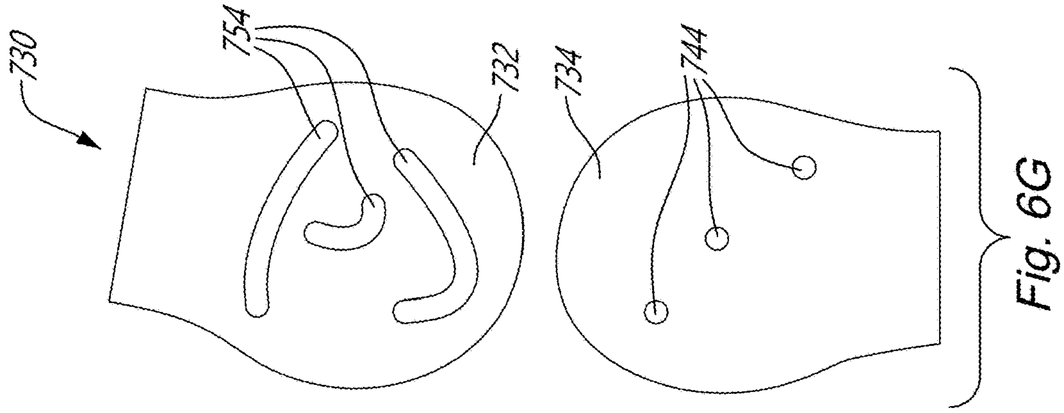
FIGS. 6D-6G show side views of exemplary hinge configurations, showing both a femoral portion and a tibial portion of each hinge configuration, having different combinations and permutations of three pins and three slots.
Figure 6F:
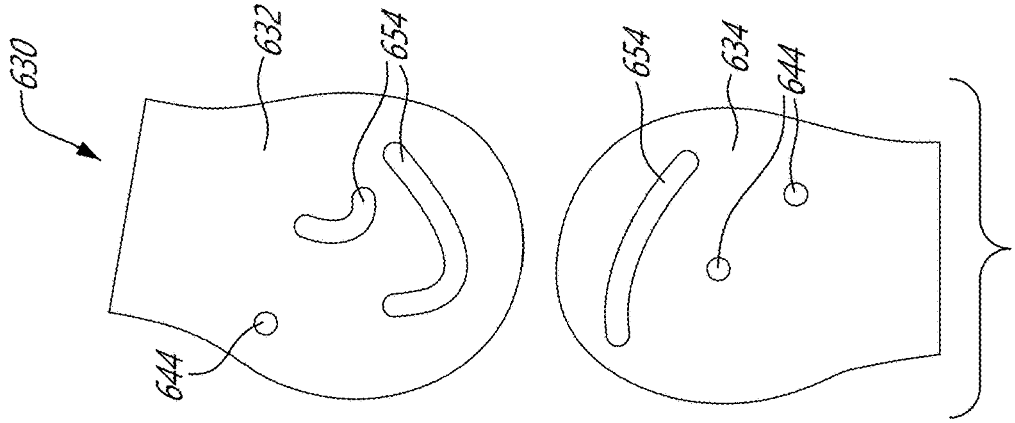
Figure 6E:
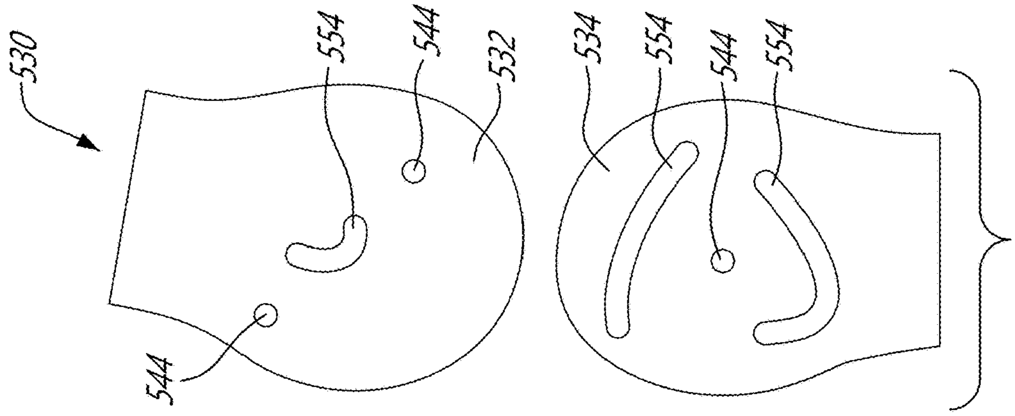
Figure 6D:
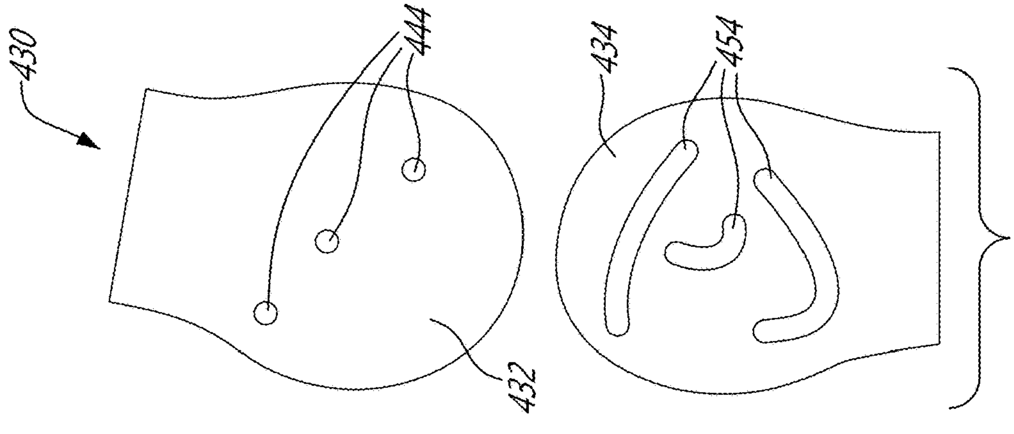

Referring now to FIGS. 6D-6G, four other hinge configurations are depicted, each having a different configuration and permutation of three guide slots and three pins. In the embodiment of FIG. 6D, the hinge 430 includes three guide slots 454 all located in the tibial portion 434 and three pins 444 located on the femoral portion 432. In the embodiment of FIG. 6E, the hinge 530 includes three guide slots 554, two guide slots 554 located in the tibial portion 534 and one guide slot 554 located in the femoral portion 532, and three pins 544, one pin 544 located in the tibial portion 534 and two pins 544 located in the femoral portion 532. In the embodiment of FIG. 6F, the hinge 630 includes three guide slots 654, two guide slots 654 located in the femoral portion 632 and one guide slot 654 located in the tibial portion 634, and three pins 644, one pin 644 located in the femoral portion 632 and two pins 644 located in the tibial portion 634. In the embodiment of FIG. 6G, the hinge 730 includes three guide slots 754 all located in the femoral portion 732 and three pins 744 all located on the tibial portion 734. Each of these hinge configurations can also be inversed (e.g., the elements located on the tibial portion being located on the femoral portion, and vice versa). It is also to be understood that these examples are but four possible hinge configurations, and that other alternate configurations and permutations are possible without departing from the scope of the present disclosure.

Design considerations may also be considered, for example to ensure a suitable compromise between various parameters which may be considered, including for example stability, movement control, range of motion, size of the hinge, number of parts required, etc. In the depicted embodiments, three slots and three corresponding pins are shown. The mating slot(s) and pin(s), regardless of the number of slots and pins, serve to guide a pivoting movement of the femoral and tibial portions relative to each other. Thus, one of the femoral and tibial portions of the hinge has at least one guide slot defined in a corresponding shell, and the other one of the femoral portion and the tibial portion has at least one pin extending in the at least one guide slot. In most embodiments, however, two or three guide slots and corresponding pins are likely to be used, although a single slot/pin or more than three slots/pins could also be used.

Figure 7C:
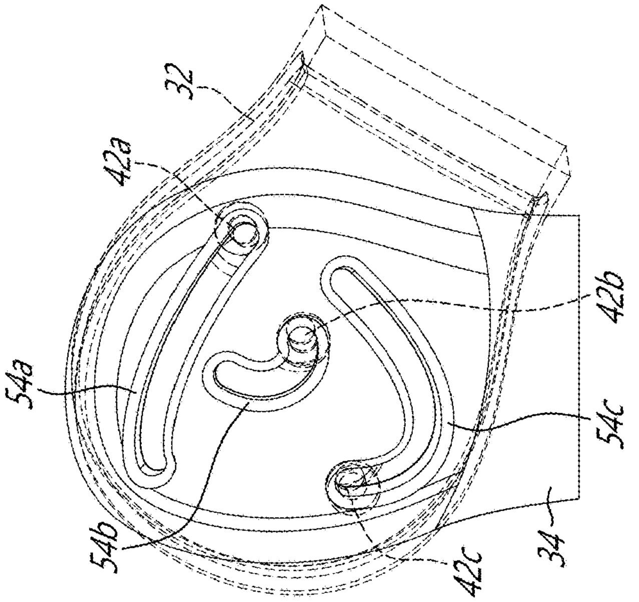
FIG. 7C is a side view of the hinges of FIG. 7A in a 120° flexion configuration.
Figure 7B:
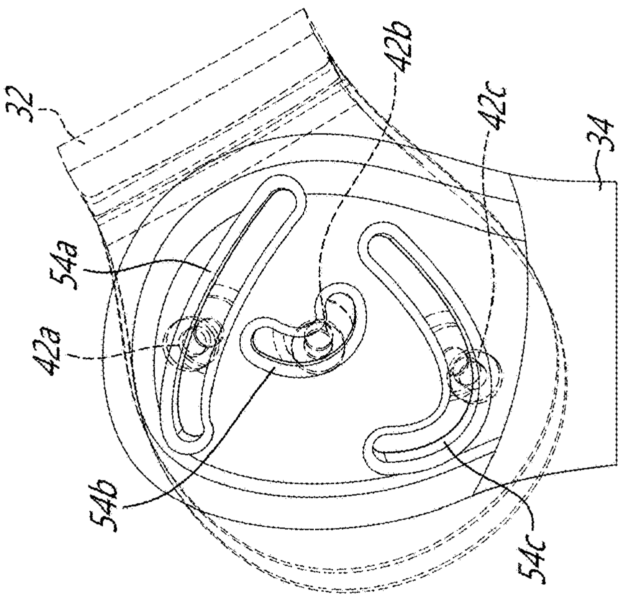
FIG. 7B is a side view of the hinges of FIG. 7A in a 60° flexion configuration.
Figure 7A:
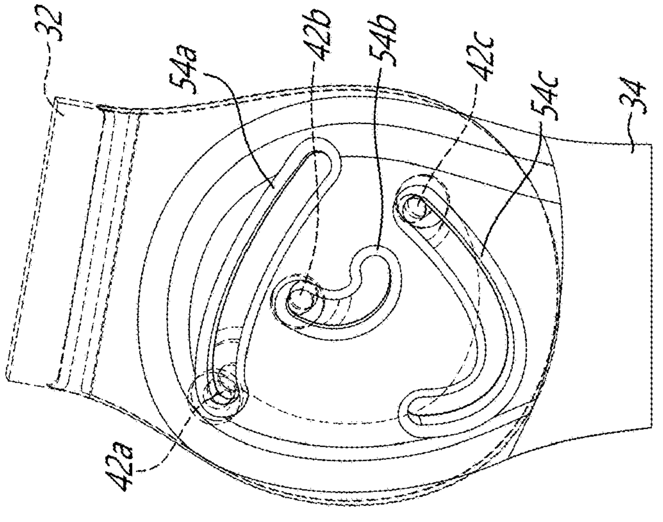
FIG. 7A is a side view of the hinges of FIG. 3A in a 10° flexion configuration, with the femoral portion shown in transparency.

Referring to FIGS. 7A-7C, the cooperation between the pins 44*a*, 44*b*, 44*c* (omitted herein for clarity, the holes 42*a*, 42*b*, 42*c* being shown instead) and the corresponding guiding slots 54*a*, 54*b*, 54*c* is shown during flexion of the knee orthosis 20. The pins 44*a*, 44*b*, 44*c* are fixed relative to the femoral shells 40*a*, 40*b*, and the guiding slots 54*a*, 54*b*, 54*c* allow the shells 50*a*, 50*b* to move relative to the shells 40*a*, 40*b* while being guided by the guiding slots 54*a*, 54*b*, 54*c*.

Figure 8A:
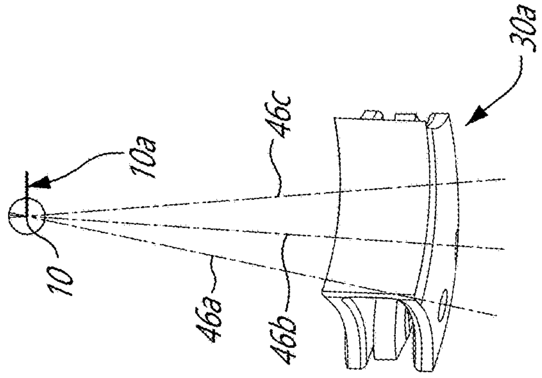
FIG. 8A is a top view of the lateral hinge of FIG. 3A in a 10° flexion configuration, with pin axes converging to an instantaneous center of rotation of the knee.
Figure 8B:
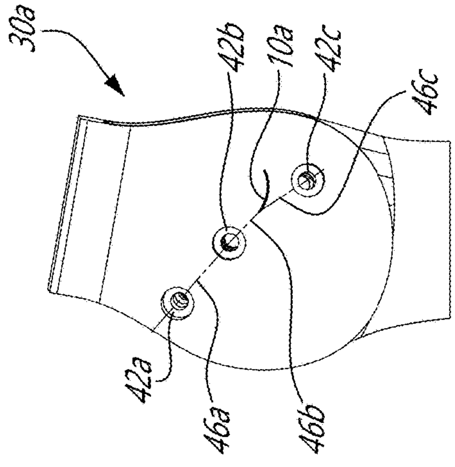
FIG. 8B is a side view of the lateral hinge of FIG. 8A.
Figure 8C:
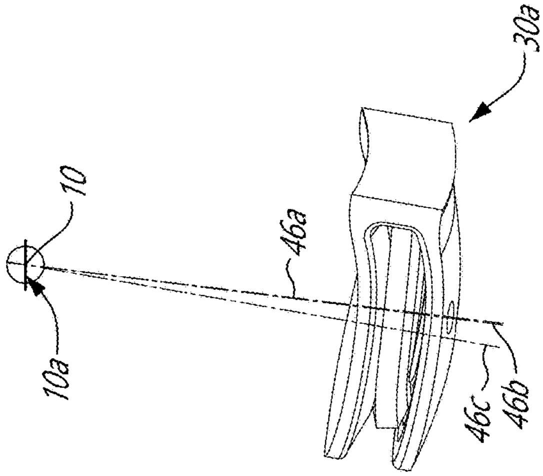
FIG. 8C is a top view of the lateral hinge of FIG. 3A in a 60° flexion configuration, with pin axes converging to an instantaneous center of rotation of the knee.
Figure 8D:
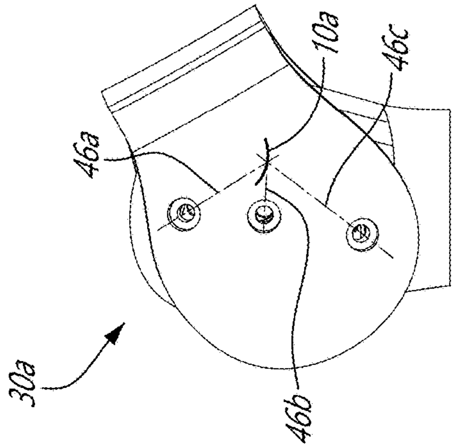
FIG. 8D is a side view of the lateral hinge of FIG. 8C.
Figure 8E:
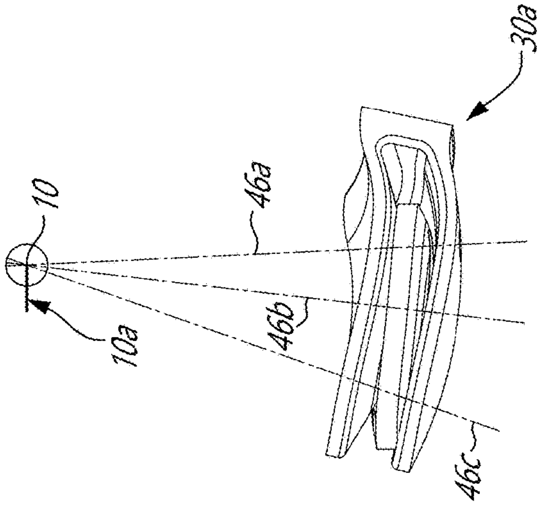
FIG. 8E is a top view of the lateral hinge of FIG. 3A in a 120° flexion configuration, with pin axes converging to an instantaneous center of rotation of the knee.
Figure 8F:
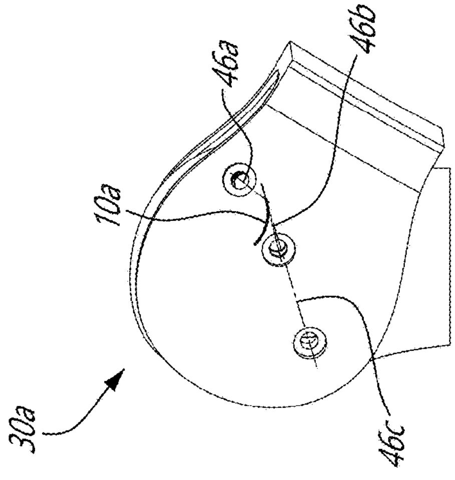
FIG. 8F is a side view of the lateral hinge of FIG. 8E.

Referring to FIGS. 8A-8F, the pin axes 46*a*, 46*b*, 46*c* are shown extending through the hinge 30*a* toward the center of rotation 10 of the knee. More particularly, in FIGS. 8A-8B, the hinge 30*a* is at 10° of flexion, and the axes 46*a*, 46*b*, 46*c* converge and intersect the center of rotation 10 of the knee for this instantaneous flexion angle. In FIGS. 8C-8D, the hinge 30*a* is at 60° of flexion, and the axes 46*a*, 46*b*, 46*c* converge and intersect the center of rotation 10 of the knee for this instantaneous flexion angle. Similarly, in FIGS. 8E-8F, the hinge 30*a* is at 120° of flexion, and the axes 46*a*, 46*b*, 46*c* converge and intersect the center of rotation 10 of the knee for this instantaneous flexion angle. As seen in FIGS. 8A, 8C and 8E, the instantaneous center of rotation 10 moves along the trajectory 10*a* contained in the sagittal plane 12 (see FIG. 9A) during flexion of the hinge 30*a*, and the axes 46*a*, 46*b*, 46*c* all converge and intersect the instantaneous center of rotation 10 regardless of the flexion angle of the hinge 30*a* (i.e., at all flexion angles of the hinge 30*a*, the axes 46*a*, 46*b*, 46*c* will intersect the corresponding instantaneous center of rotation 10). Put differently, the shape of the shells 40*a*, 40*b*, 50*a*, 50*b* and the configuration of the pins 44*a*, 44*b*, 44*c* and guiding slots 54*a*, 54*b*, 54*c* allow for the hinge 30*a* to follow the knee's center of rotation 10 throughout a range of flexion of the knee orthosis 20. This feature may assist the knee orthosis in allowing femoral roll back and screw home motions during flexion and extension of the knee.

Figure 9B:
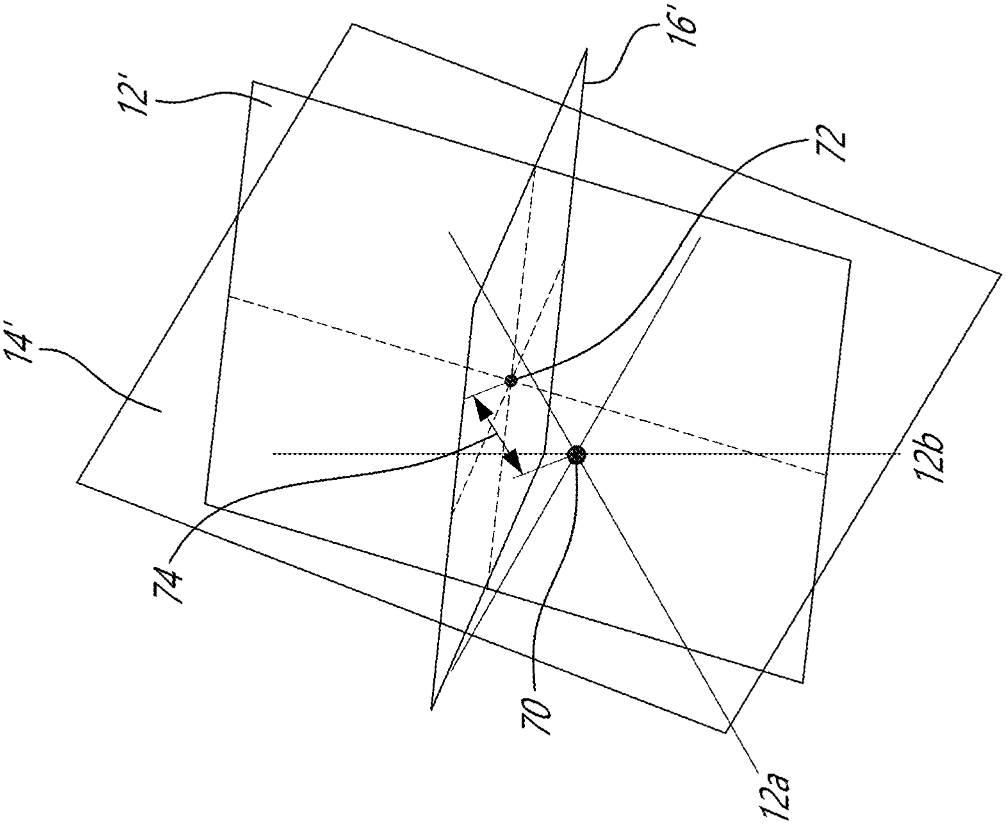
FIG. 9B is an isometric view of the planes of FIG. 9A translated to a mid-flexion position.
Figure 9A:
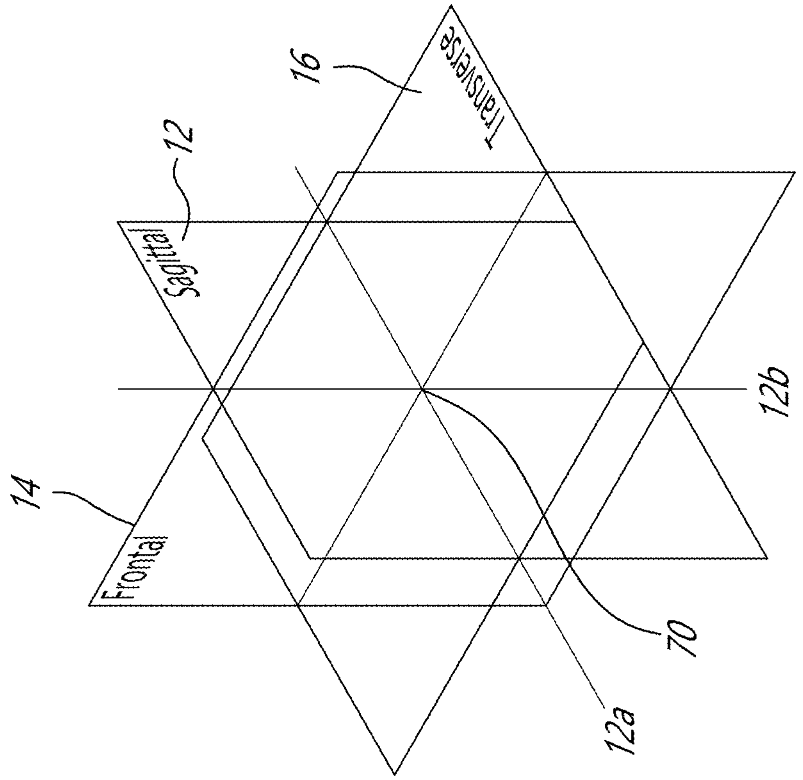
FIG. 9A is an isometric view of a sagittal plane, a frontal plane and a transversal plane in an initial position.

Referring now to FIGS. 9A-9D, there is shown how the ellipsoid 60 is formed for designing the shells 40*a*, 40*b*, 50*a*, 50*b*. In FIG. 9A, the sagittal plane 12, the frontal plane 14, and the transversal plane 16 are shown in their initial positions, corresponding to a 0° of flexion of the knee and knee orthosis 20. An initial origin 70 exists at the intersection of the planes 12, 14, 16 and corresponds to the COR 10 at 0° of flexion.

In FIG. 9B, the coordinate system defined by the sagittal, frontal and transversal planes, namely planes 12, 14, 16 respectively, is translated and transformed (i.e., pivoted) to match a chosen position along the flexion trajectory of the knee. Consequently, the translated and pivoted planes are shown by planes 12', 14', 16', wherein the frontal plane 14' is disposed at a pre-determined flexion angle, which is about 60° in the represented implementation, relative to the initial position of the frontal plane 14 with respect to the sagittal plane 12. The pre-determined translation and rotation angle are selected, in the present implementation, to correspond to a mid-point flexion configuration of the knee, with the coupled abduction and rotation angles corresponding to this mid-point flexion configuration. In the present implementation, there is a coupled external rotation of about 6 degrees and an abduction value of about 4 degrees.

The planes 12', 14', 16' are also translated along the anteroposterior axis 12*a* (see FIG. 9C) and the inferior-superior axis 12*b* that is contained in the sagittal plane 12. A translation of the initial origin 70 corresponds to the COR 10 translation occurring at the mid-point flexion configuration of the knee. A translated origin 72 exists at the intersection of the moved planes 12', 14', 16', i.e. translated and rotated as described above, and corresponds to the position of the COR 10 at 60° of flexion. An anteroposterior and infero-superior shift 74 correspond to a distance between the translated origin 72 and the initial origin 70. The shift 74 corresponds to a displacement of the knee's COR 10 along the trajectory 10*a* between the initial origin 70 to the translated origin 72. In the present implementation, the planes 12', 14', 16' are translated by about 4 mm in a posterior direction, and by about 3 mm in an inferior direction. At this specific chosen flexion configuration, that is at the mid-point flexion configuration, the tibial ellipsoid will perfectly match the femoral ellipsoid thereby resulting in minimal to no deformation of the shells.

Other pre-determined angles are contemplated. For example, in a particular embodiment the pre-determined angle is between 40 and 80 degrees, inclusively (i.e., including both 40 degrees and 80 degrees). Alternately, the pre-determined angle may range between 30° and 90°, inclusively, or between 20° and 100°, inclusively. However, the pre-determined angle of about 60° may be preferably selected so as to have the ellipsoidal shells 40*a*, 40*b*, 50*a*, 50*b* with reduced interference therebetween at a flexion angle of 60° compared to a starting point flexion configuration (i.e. 0° of flexion) and to an end point flexion configuration (i.e. 120° of flexion). The end point flexion configuration could differ in other implementations and be at more than 120° of flexion. Additionally, in certain embodiments the staring point flexion configuration may be selected not to start at 0° of flexion, for example to prevent hyper-extension.

Figure 9D:
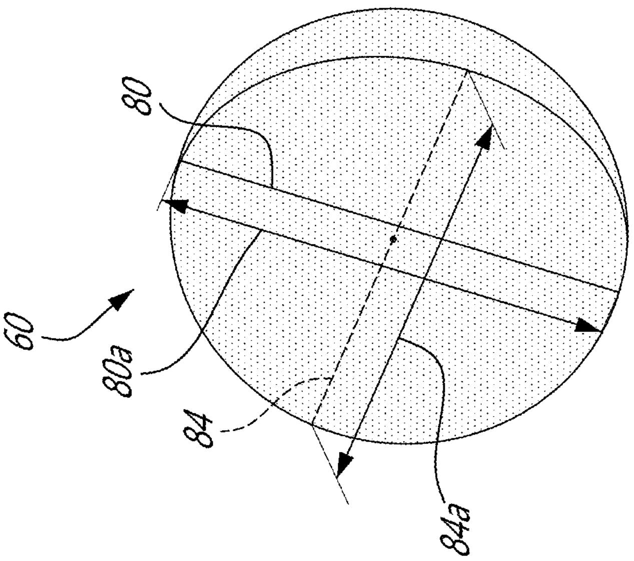
FIG. 9D is an isometric view of an ellipsoid defined by revolution around the major axis of FIG. 9C and the minor axis of FIG. 9C.
Figure 9C:
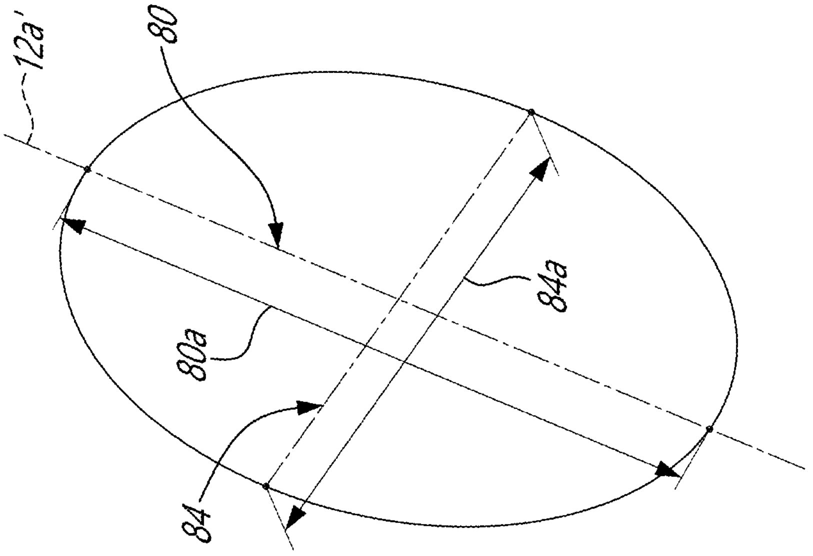
FIG. 9C is an isometric view of major and minor axes corresponding to axes defined by planes of FIG. 9B.

In FIG. 9C, a major axis 80 is defined as corresponding to the tilted anteroposterior axis 12*a*', which is defined by the tilted planes 12', 14', 16'. The ellipsoid 60 accordingly has a length 80*a* along the major axis 80, and a width 84*a* along a minor axis 84. The minor axis 84 is orthogonal to the major axis 80. The width 84*a* of the minor axis 84 is based on a morphologic feature of the knee of the wearer, such as a width of the knee of the wearer. In one implementation, the width 84*a* corresponds to the distance 82 between the hinges 30*a*, 30*b*. The length 80*a* of the major axis 80 corresponds to the width of the minor axis 84*a* plus the anteroposterior shift 74 of the COR 10 along trajectory 10*a*. In one implementation, therefore, the length 80*a* corresponds to a distance 82 (FIG. 2) between the hinges 30*a*, 30*b* plus the anteroposterior shift 74. The distance 82 is based on a morphologic feature of the knee of the wearer, such as a width of the knee of the wearer. Put differently, the minor axis 84 corresponds to the width of the knee and the major axis 80 corresponds to the minor axis 84 plus the anteroposterior shift 74, and therefore the major axis 80 is longer than the minor axis 84 by an amount corresponding to the anteroposterior shift 74.

Referring to FIG. 9D, the ellipsoid 60 is obtained by revolution around the major axis 80, with lengths 80*a*, 84*a* along the major axis 80 and minor axis 84 respectively. The resulting ellipsoid 60 is based a morphologic feature of the knee of the wearer, such as a width of the knee of the wearer.

Figure 10C:
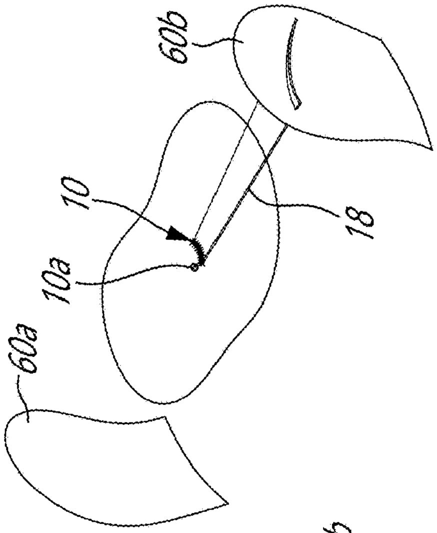
FIG. 10C is an isometric view of the tibial plateau and shells of the hinges, with instantaneous flexion axes projected on the shells.
Figure 10B:
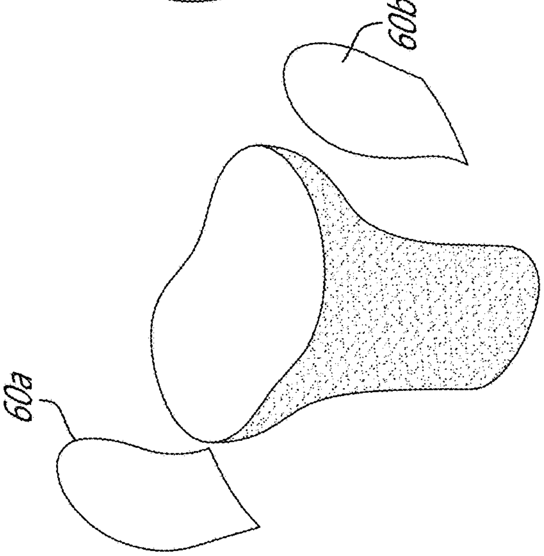
FIG. 10B is an isometric view of the tibial plateau and portions of the ellipsoid defining shells of the hinges.
Figure 10A:
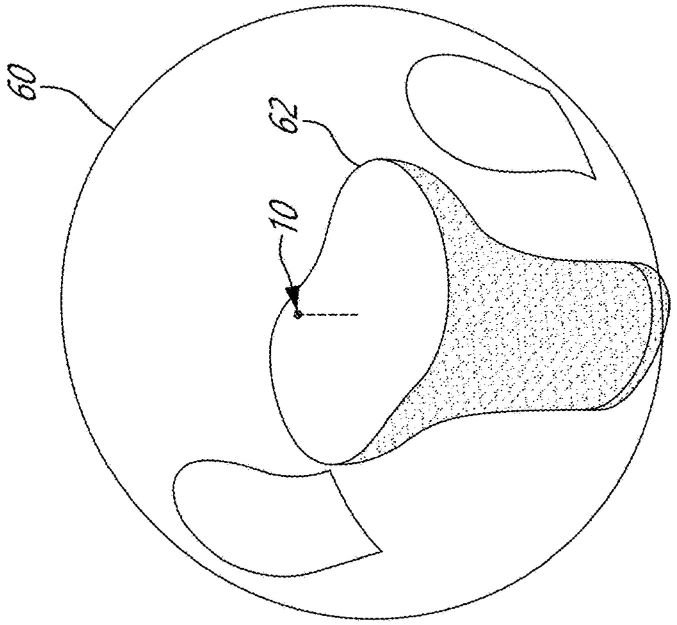
FIG. 10A is an isometric view of the ellipsoid of FIG. 9D shown in transparency and centered on a center of rotation of the knee at a tibial plateau.

Referring to FIGS. 10A-10B, the ellipsoid 60 is superposed in FIG. 10A with a model of a tibial plateau 62 of the wearer, with a center of the ellipsoid 60 located an instantaneous COR 10 of the knee flexed at 60°. In FIG. 10B, portions 60*a*, 60*b* of the ellipsoid 60 are isolated to define the shape of the ellipsoidal shells 40*a*, 40*b*, 50*a*, 50*b*. In FIG. 10C, there is shown that the instantaneous flexion axes 18 for a range of motion of the hinges 30*a*, 30*b* (for example, between 0° and 120°) are projected on the ellipsoidal shell portions 60*a*, 60*b* to define the guiding slot 54*a*. Once the ellipsoidal shape 60 of the shells 40*a*, 40*b*, 50*a*, 50*b* is defined, the shells 40*a*, 40*b*, 50*a*, 50*b* may be dimensioned and/or adapted to conform to morphologic feature(s) of the wearer.

Having hinges 30*a*, 30*b* with ellipsoidal shells 40*a*, 40*b*, 50*a*, 50*b* (i.e. shells having a shape corresponding to a portion of an ellipsoid such as ellipsoid 60) presents some advantages over a hinge having shells that corresponds to an arc of a sphere, i.e. where the curvature radius is constant on the surface of the shell. A hinge having shells that corresponds to an arc of a sphere accommodates pure rotation, but may not accommodate for rotation and simultaneous translation motions, as occurring during the flexion of a knee. For instance, embedded spherical shells accommodate rotation in three relative orientations, but do not accommodate for translation motions therebetween. In contrast, having a hinge with shells corresponding to a portion of an ellipsoid can better accommodate rotations combined with translation motions that occur during flexion of a knee.

Figure 13A:
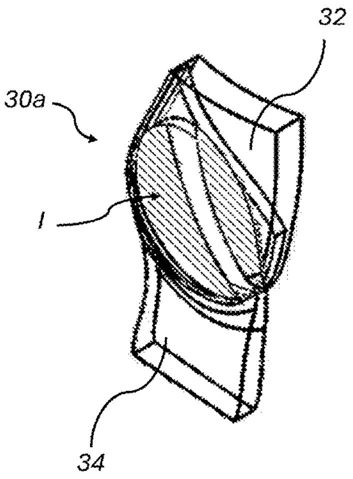
FIGS. 13A-13C are side views of one of the hinges of FIG. 3A, shown in different flexion configurations.
Figure 13B:
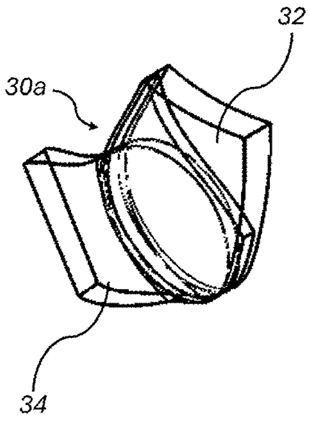
Figure 13C:
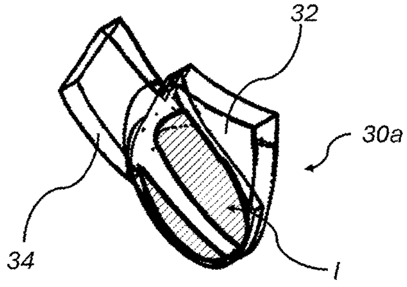

As best seen in FIG. 1A, the COR 10 is translated along the sagittal plane 12 during flexion of the knee. In addition, and with additional reference to FIGS. 13A-13C, the ellipsoidal shells 40 *a*, 40 *b*, 50 *a*, 50 *b* are also designed to minimize interference therebetween when engaging one another at a mid-flexion point configuration of the hinges 30 *a*, 30 *b*, such as at 60° of flexion. The term "interference" (denoted by hatching labelled as "I" in FIGS. 13A-13C) as used herein in this context is defined in further detail below. Such a feature may reduce friction and/or deformation between the engagement surfaces 41, 52 at the mid-flexion point configuration of the hinges 30 *a*, 30 *b* (as shown in FIG. 13B), compared to starting point flexion configuration (i.e. 0° of flexion, as shown in FIG. 13A) and/or the end point flexion configuration (i.e. 120° of flexion, as shown in FIG. 13C). The mid-flexion point will accordingly have the least amount of interference (friction and/or deformation), as deformation increases along the delta flexion. With such a centered minimal-interference fit, the absolute deformation is limited at both the start and end points of rotation. With reduced friction comes an increase in durability and better movement control of the shells 40 *a*, 40 *b*, 50 *a*, 50 *b* as there is reduced wear of the engagement surfaces 41, 52. Portions of the ellipsoidal shells 40 *a*, 40 *b*, 50 *a*, 50 *b* may also be removed or reduced in size (e.g., trimmed, shaved off or otherwise having material removed therefrom), particularly in outer portions thereof, to further reduce unwanted deformation of the shells 40 *a*, 40 *b*, 50 *a*, 50 *b*.

Figure 11C:
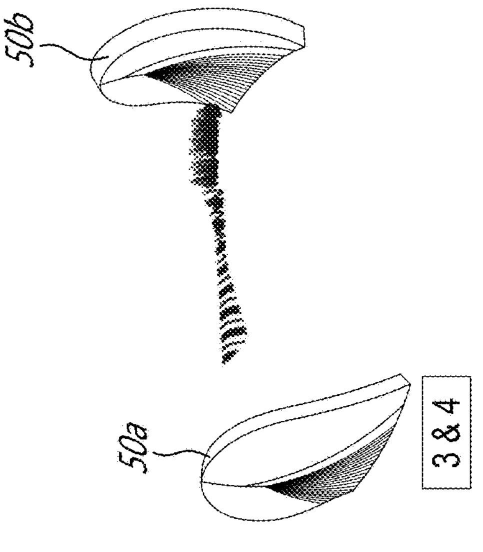
FIG. 11C is an isometric view of shells defined as a portion of an ellipsoid obtained from the circles of FIG. 11B.
Figure 11B:
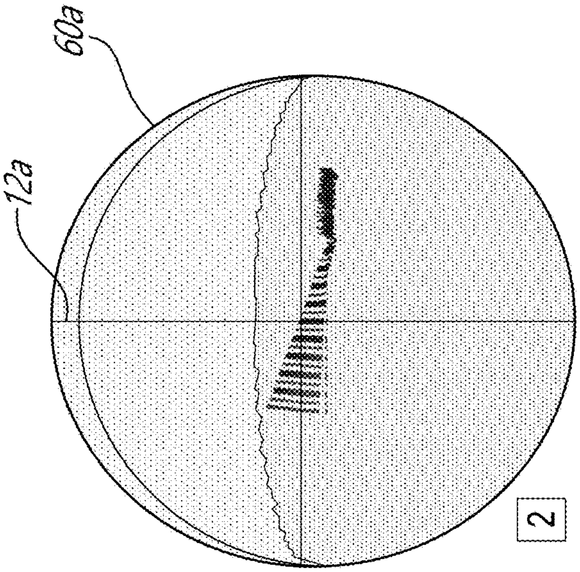
FIG. 11B is a top plan view of circles obtained with centers corresponding to 5° increments of the flexion.
Figure 11A:
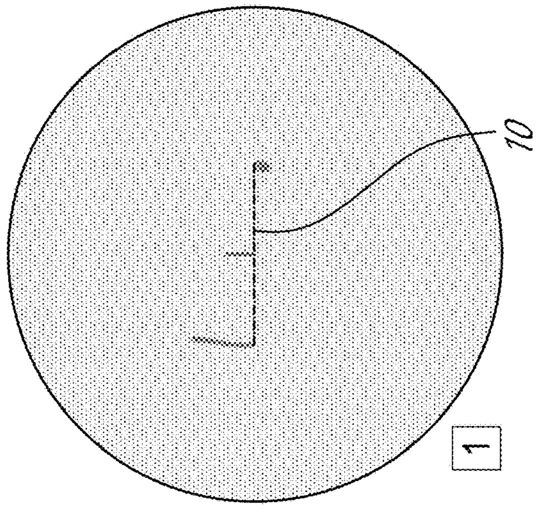
FIG. 11A is a top plan view of a circle used to define an ellipsoid with a center thereof corresponding to a COR at 0° of flexion.

In other embodiments, the shells 40*a*, 40*b*, 50*a*, 50*b* have an ellipsoid shape obtained using other construction techniques. In the implementation shown in FIGS. 11A-11C, the shells 40*a*, 40*b*, 50*a*, 50*b* correspond to a portion of an ellipsoid 60*a* (i.e. non-spherical shape with a surface that has a non-constant radius of curvature). The surface 60*a* is created by having circles defined in the transversal plane 16, with a center thereof corresponding to the COR 10. A diameter of the circle is the width of the knee. For each increment of 5°, a new circle is defined with the instantaneous COR 10, and with the same diameter corresponding to the width of the knee. In FIG. 11B, the ellipsoid 60*a* is generated by revolution around the anteroposterior axis 12*a* and by keeping the resulting exterior surfaces for defining one continuous, closed exterior surface of the ellipsoid 60*a*. In FIG. 11C, the shells 50*a*, 50*b* are obtained by isolating portions of the ellipsoid 60*a*.

Figure 12C:
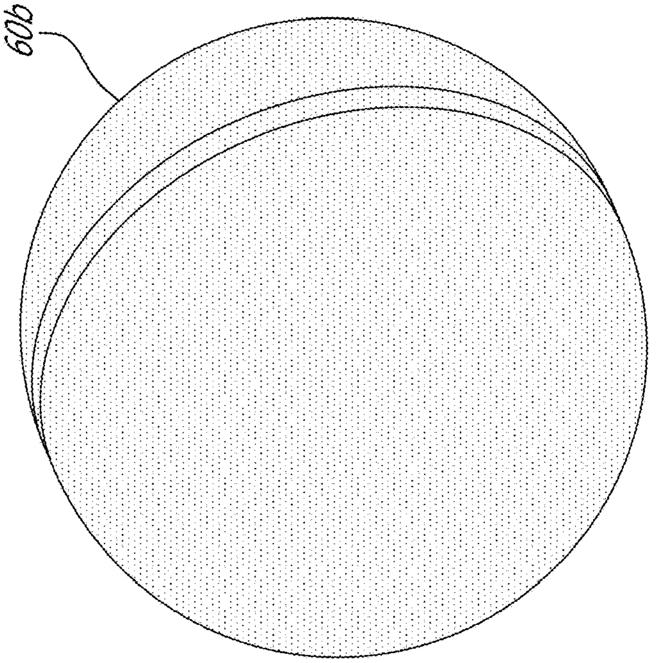
FIG. 12C is an isometric view of an ellipsoid obtained from the circles of FIG. 12A.
Figure 12B:
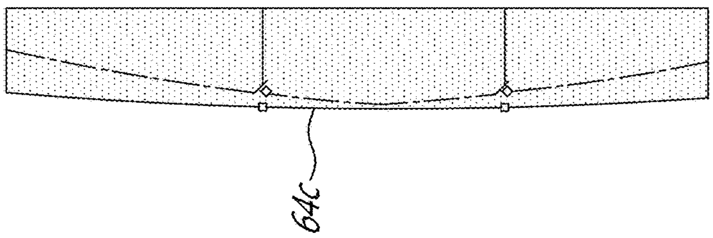
FIG. 12B is an enlarged view of region 12B in FIG. 12A.
Figure 12A:
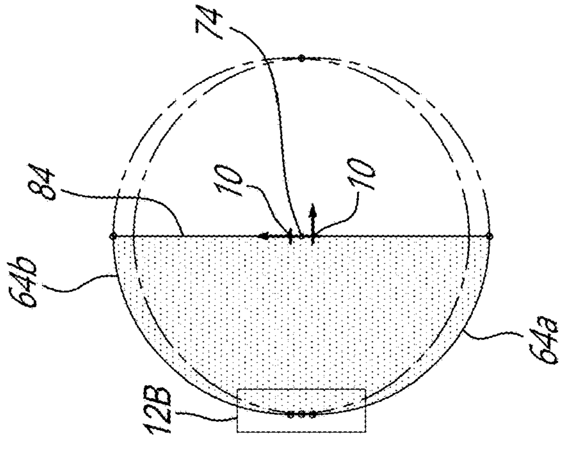
FIG. 12A is top plan view of a circle used to define an ellipsoid with a center thereof corresponding to a COR at 0° of flexion, and of another circle with a center thereof corresponding to a COR at 120° of flexion.

Turning now to FIGS. 12A-12C, a first half circle 64*a* is defined in the transversal plane 16 with a center thereof corresponding to the instantaneous COR 10 at 0° of flexion. A second half circle 64*b* is defined in the transversal plane 16 with a center thereof corresponding to the instantaneous COR 10 at 120° of flexion. The anteroposterior shift 74 exists between the two CORs 10, and a major axis 84 of the ellipsoid 60*b* is defined. The two half circles are linked together with a line 64*c* respecting tangency of both half circles. The ellipsoid 60*b* (FIG. 12C) is obtained by revolution around the major axis 84.

The term "interference" as used herein is understood to mean contact between surfaces, and this contact may in certain instances generate friction and/or may cause deformation of one or more the surfaces or parts of the respective elements which are in contact with each other. Interference in this context does not mean that the parts or surfaces occupy the same volume in three-dimensional space, but rather that friction and/or deformation occurs.

It is noted that various connections are set forth between elements in the preceding description and in the drawings. It is noted that these connections are general and, unless specified otherwise, may be direct or indirect and that this specification is not intended to be limiting in this respect. A coupling between two or more entities may refer to a direct connection or an indirect connection. An indirect connection may incorporate one or more intervening entities. The term "connected" or "coupled to" may therefore include both direct coupling (in which two elements that are coupled to each other contact each other) and indirect coupling (in which at least one additional element is located between the two elements).

As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

While various aspects of the present disclosure have been disclosed, it will be apparent to those of ordinary skill in the art that many more embodiments and implementations are possible within the scope of the present disclosure. For example, the present disclosure as described herein includes several aspects and embodiments that include particular features. Although these particular features may be described individually, it is within the scope of the present disclosure that some or all of these features may be combined with any one of the aspects and remain within the scope of the present disclosure. References to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. The use of the indefinite article "a" as used herein with reference to a particular element is intended to encompass "one or more" such elements, and similarly the use of the definite article "the" in reference to a particular element is not intended to exclude the possibility that multiple of such elements may be present. Additionally, the expression "at least one of" as used herein is understood to mean "one or both of", or alternately stated "and/or". In other words, the expression "at least one of X and Y" is understood to mean: just X; just Y; or both X and Y.

The embodiments described in this document provide non-limiting examples of possible implementations of the present technology. Upon review of the present disclosure, a person of ordinary skill in the art will recognize that changes may be made to the embodiments described herein without departing from the scope of the present technology. Yet further modifications could be implemented by a person of ordinary skill in the art in view of the present disclosure, which modifications would be within the scope of the present technology.

The invention claimed is:

1. A knee orthosis comprising:

a femoral cuff configured for engaging an upper leg of a wearer;

a tibial cuff configured for engaging a lower leg of the wearer;

a hinge pivotally connecting the femoral cuff to the tibial cuff, the hinge having a femoral portion connected to the femoral cuff and a tibial portion connected to the tibial cuff, the femoral portion and the tibial portion including respective shells engaged with one another and configured to pivot relative to one another about a center of rotation, a first one of the shells including an engagement surface facing a complementary engagement surface on a second one of the shells, the engagement surface and the complementary engagement surface each having a non-spherical surface curvature corresponding to a portion of an ellipsoid, the ellipsoid defined by:

a major axis extending in a sagittal plane;

a minor axis orthogonal to the major axis;

a length of the ellipsoid along the major axis being greater than a length along the minor axis; and revolution around the major axis.

2. The knee orthosis of claim 1, wherein one of the femoral portion and the tibial portion of the hinge has at least one guide slot defined in the corresponding shell, another one of the femoral portion and the tibial portion has at least one pin extending in the at least one guide slot for guiding a pivot of the femoral and tibial portions relative to one another, the at least one pin defining an axis intersecting a center of rotation of a knee of the wearer.

3. The knee orthosis of claim 2, wherein: the hinge includes two or three guide slots and two or three pins; said two or three guide slots being located on the femoral portion, the tibial portion or a combination of the two; and said two or three pins being located on the femoral portion, the tibial portion or a combination of the two.

4. The knee orthosis of claim 2, wherein the femoral portion of the hinge has at least one guide slot and at least one pin, and the tibial portion of the hinge has at least one guide slot and at least one pin.

5. The knee orthosis of claim 2, wherein the center of rotation is an instantaneous center of rotation at a given flexion configuration of the hinge, the instantaneous center of rotation moving along a trajectory during flexion of the hinge, and wherein the axis defined by the at least one pin intersects the instantaneous center of rotation regardless of the flexion configuration of the hinge.

6. The knee orthosis of claim 1, wherein the major axis corresponds to an anteroposterior axis, and the major axis is disposed in the sagittal plane at a pre-determined angle relative to a frontal plane orthogonal to the sagittal plane.

7. The knee orthosis of claim 6, wherein the pre-determined angle is between 40 and 80 degrees.

8. The knee orthosis of claim 1, wherein the length of the ellipsoid along the minor axis is determined based on a morphologic feature of a knee of the wearer.

9. The knee orthosis of claim 8, wherein the morphologic feature is a width of the knee of the wearer.

10. The knee orthosis of claim 1, wherein the center of rotation is an instantaneous center of rotation at a given flexion configuration of the hinge, the instantaneous center of rotation moving along a trajectory during flexion of the hinge.

11. The knee orthosis of claim 10, wherein the trajectory is contained in the sagittal plane.

12. The knee orthosis of claim 1, wherein the length of the ellipsoid along the major axis is greater than the length of the ellipsoid along the minor axis by an amount corresponding to an anteroposterior shift of a center of rotation of the knee.

13. The knee orthosis of claim 1, wherein, at a mid-flexion point configuration of the hinge, the shells have a first interference therebetween, at a starting point flexion configuration, the shells have a second interference therebetween;

at an end point flexion configuration, the shells have a third interference therebetween; and the first interference is smaller than at least one of the second and third interference.

14. A knee orthosis comprising:

a femoral cuff configured for engaging an upper leg of a wearer;

a tibial cuff configured for engaging a lower leg of the wearer; and a hinge pivotally connecting the femoral cuff to the tibial cuff, the hinge having a femoral portion connected to the femoral cuff and a tibial portion connected to the tibial cuff, the femoral portion and the tibial portion including corresponding shells engaged with one another and configured to pivot relative to one another about a center of rotation, one of the femoral portion and the tibial portion has at least one guide slot defined in the corresponding shell, and the other of the femoral portion and the tibial portion has at least one pin extending therefrom and received within the at least one guide slot for guiding the pivot of the femoral and tibial portions relative to one another, the at least one pin defining a pin axis intersecting a center of rotation of a knee of the wearer;

wherein the shells include complementary engagement surfaces facing each other, the complementary engagement surfaces having a non-spherical surface curvature corresponding to a portion of an ellipsoid, the ellipsoid defined by:

a major axis extending in a sagittal plane;

a minor axis orthogonal to the major axis;

a length of the ellipsoid along the major axis being greater than a length along the minor axis; and revolution around the major axis.

15. The knee orthosis of claim 14, wherein the length of the ellipsoid along the minor axis corresponds to a morphologic feature of a knee of the wearer.

16. The knee orthosis of claim 15, wherein the morphologic feature is a width of the knee of the wearer.

17. The knee orthosis of claim 15, wherein the length of the ellipsoid along the major axis is greater than the length of the ellipsoid along the minor axis by an amount corresponding to an anteroposterior shift of the center of rotation of the knee.

18. The knee orthosis of claim 14, wherein the center of rotation is an instantaneous center of rotation at a given flexion configuration of the hinge, the instantaneous center of rotation moving along a trajectory during flexion of the hinge, and the pin axis intersecting the instantaneous center of rotation regardless of the flexion configuration of the hinge.

19. The knee orthosis of claim 18, wherein the trajectory is contained in a sagittal plane.

20. The knee orthosis of claim 14, wherein the major axis corresponds to an anteroposterior axis, and the major axis is disposed in the sagittal plane at a pre-determined angle relative to a frontal plane orthogonal to the sagittal plane.

21. The knee orthosis of claim 20, wherein the pre-determined angle is between 40 and 80 degrees.

22. The knee orthosis of claim 14, wherein, at a mid-flexion point configuration of the hinge, the shells have a first interference therebetween, at a starting point flexion configuration, the shells have a second interference therebetween;

at an end point flexion configuration, the shells have a third interference therebetween; and the first interference is smaller than at least one of the second and third interference.

23. A knee orthosis comprising:

a femoral cuff configured for engaging an upper leg of a wearer;

a tibial cuff configured for engaging a lower leg of the wearer;

a hinge pivotally connecting the femoral cuff to the tibial cuff, the hinge having a femoral portion connected to the femoral cuff and a tibial portion connected to the tibial cuff, the femoral portion and the tibial portion including respective shells engaged with one another and configured to pivot relative to one another about a center of rotation, a first one of the shells including an engagement surface facing a complementary engagement surface on a second one of the shells, the engagement surface and the complementary engagement surface each having a shape corresponding to a portion of an ellipsoid defined by:

a major axis extending in a sagittal plane;

a minor axis orthogonal to the major axis;

a length of the ellipsoid along the major axis being greater than a length along the minor axis; and revolution around the major axis;

wherein the length of the ellipsoid along the major axis is greater than the length of the ellipsoid along the minor axis by an amount corresponding to an anteroposterior shift of a center of rotation of the knee.

* * * * *